(12) United States Patent
Swanson et al.

(10) Patent No.: US 8,925,191 B2
(45) Date of Patent: Jan. 6, 2015

(54) METHOD OF FABRICATING A STIMULATION LEAD

(75) Inventors: John Swanson, Portland, OR (US); Kevin Turner, Frisco, TX (US); Jerome Boogaard, Forest Grove, OR (US)

(73) Assignee: Advanced Neuromodulation Systems, Inc., Plano, TX (US)

( * ) Notice: Subject to any disclaimer, the term of this patent is extended or adjusted under 35 U.S.C. 154(b) by 421 days.

(21) Appl. No.: 13/449,717

(22) Filed: Apr. 18, 2012

(65) Prior Publication Data

US 2012/0198694 A1 Aug. 9, 2012

Related U.S. Application Data

(63) Continuation of application No. 12/895,466, filed on Sep. 30, 2010, now Pat. No. 8,171,621.

(60) Provisional application No. 61/247,320, filed on Sep. 30, 2009.

(51) Int. Cl.
*H05K 3/02* (2006.01)
*H01R 13/03* (2006.01)
*A61N 1/05* (2006.01)
*H01R 24/58* (2011.01)
*H01R 107/00* (2006.01)

(52) U.S. Cl.
CPC .............. *A61N 1/05* (2013.01); *H01R 2201/12* (2013.01); *H01R 24/58* (2013.01); *H01R 13/035* (2013.01); *H01R 2107/00* (2013.01)
USPC ................. 29/846; 29/825; 29/847; 600/374; 607/122

(58) Field of Classification Search
USPC .............. 29/825, 846, 847; 600/374; 607/122
See application file for complete search history.

(56) References Cited

U.S. PATENT DOCUMENTS

| 5,462,545 | A | 10/1995 | Wang et al. |
| 5,649,970 | A | 7/1997 | Loeb et al. |
| 5,855,552 | A * | 1/1999 | Houser et al. ................ 600/374 |
| 6,038,480 | A | 3/2000 | Hrdlicka et al. |
| 6,064,905 | A | 5/2000 | Webster, Jr. et al. |
| 6,208,881 | B1 * | 3/2001 | Champeau .................... 600/374 |
| 6,249,708 | B1 * | 6/2001 | Nelson et al. ................ 607/122 |
| 6,473,653 | B1 | 10/2002 | Schallhorn et al. |
| 6,757,970 | B1 * | 7/2004 | Kuzma et al. .................. 29/847 |
| 7,047,081 | B2 * | 5/2006 | Kuzma .......................... 607/115 |
| 7,047,627 | B2 * | 5/2006 | Black et al. ..................... 29/825 |
| 7,200,446 | B2 | 4/2007 | Borkan |
| 7,212,867 | B2 | 5/2007 | Van Venroo |
| 7,668,601 | B2 | 2/2010 | Hegland et al. |
| 7,761,985 | B2 | 7/2010 | Hegland et al. |

(Continued)

*Primary Examiner* — Carl Arbes (57) ABSTRACT

In one embodiment, a method of fabrication of a stimulation lead comprising a plurality of segmented electrodes for stimulation of tissue of a patient, the method comprises: providing an elongated, substantially cylindrical substrate, the substrate comprising a plurality of recesses defined in an outer surface of the substrate; coating the substrate with conductive material; patterning conductive material on the substrate to form a plurality of electrode surfaces for at least the plurality of segmented electrodes and a plurality of traces connected to the plurality of electrode surfaces, wherein each electrode surface and its corresponding trace are defined in the recesses on the outer surface of the substrate and are electrically isolated from other electrode surfaces and traces; providing insulative material over at least the plurality of traces; and electrically coupling the plurality of traces to conductive wires of a lead body.

19 Claims, 9 Drawing Sheets

(56) References Cited

U.S. PATENT DOCUMENTS

| | | |
|---|---|---|
| 7,792,590 B1 | 9/2010 | Pianca et al. |
| 7,899,548 B2 | 3/2011 | Barker |
| 2002/0183817 A1 | 12/2002 | Van Venrooij et al. |
| 2003/0120328 A1 | 6/2003 | Jenkins et al. |
| 2005/0060885 A1 | 3/2005 | Johnson et al. |
| 2005/0131513 A1 | 6/2005 | Myers |
| 2005/0246004 A1 | 11/2005 | Cameron et al. |
| 2006/0058588 A1 | 3/2006 | Zdeblick |
| 2006/0173262 A1 | 8/2006 | Hegland et al. |
| 2007/0161294 A1* | 7/2007 | Brase et al. ............ 439/668 |
| 2007/0219595 A1* | 9/2007 | He ............................ 607/36 |
| 2008/0039916 A1 | 2/2008 | Colliou et al. |
| 2008/0114230 A1 | 5/2008 | Addis |
| 2008/0215125 A1 | 9/2008 | Farah et al. |
| 2008/0255647 A1 | 10/2008 | Jensen et al. |
| 2009/0012591 A1 | 1/2009 | Barker |
| 2010/0076535 A1 | 3/2010 | Pianca et al. |
| 2010/0100152 A1 | 4/2010 | Martens et al. |
| 2011/0072659 A1 | 3/2011 | Swanson et al. |
| 2011/0165785 A1 | 7/2011 | Lindner et al. |

* cited by examiner

METHOD OF FABRICATING A STIMULATION LEAD

CROSS-REFERENCE TO RELATED APPLICATIONS

This application is a continuation of U.S. application Ser. No. 12/895,466, filed on Sep. 30, 2010, now U.S. Pat. No. 8,171,621, which claims the benefit of U.S. Provisional Application No. 61/247,320, filed Sep. 30, 2009, which is incorporated herein by reference.

TECHNICAL FIELD

This application is generally related to stimulation leads, and in particular to stimulation leads with segmented electrodes and methods of fabrication.

BACKGROUND INFORMATION

Deep brain stimulation (DBS) refers to the delivery of electrical pulses into one or several specific sites within the brain of a patient to treat various neurological disorders. For example, deep brain stimulation has been proposed as a clinical technique for treatment of chronic pain, essential tremor, Parkinson's disease (PD), dystonia, epilepsy, depression, obsessive-compulsive disorder, and other disorders.

A deep brain stimulation procedure typically involves first obtaining preoperative images of the patient's brain (e.g., using computer tomography (CT) or magnetic resonance imaging (MRI)). Using the preoperative images, the neurosurgeon can select a target region within the brain, an entry point on the patient's skull, and a desired trajectory between the entry point and the target region. In the operating room, the patient is immobilized and the patient's actual physical position is registered with a computer-controlled navigation system. The physician marks the entry point on the patient's skull and drills a burr hole at that location. Stereotactic instrumentation and trajectory guide devices are employed to control of the trajectory and positioning of a lead during the surgical procedure in coordination with the navigation system.

Brain anatomy typically requires precise targeting of tissue for stimulation by deep brain stimulation systems. For example, deep brain stimulation for Parkinson's disease commonly targets tissue within or close to the subthalamic nucleus (STN). The STN is a relatively small structure with diverse functions. Stimulation of undesired portions of the STN or immediately surrounding tissue can result in undesired side effects. Mood and behavior dysregulation and other psychiatric effects have been reported from stimulation of the STN in Parkinson's patients.

To avoid undesired side effects in deep brain stimulation, neurologists often attempt to identify a particular electrode for stimulation that only stimulates the neural tissue associated with the symptoms of the underlying disorder while avoiding use of electrodes that stimulate other tissue. Also, neurologists may attempt to control the pulse amplitude, pulse width, and pulse frequency to limit the stimulation field to the desired tissue while avoiding other tissue.

As an improvement over conventional deep brain stimulation leads, leads with segmented electrodes have been proposed. Conventional deep brain stimulation leads include electrodes that fully circumscribe the lead body. Leads with segmented electrodes include electrodes on the lead body that only span a limited angular range of the lead body. The term "segmented electrode" is distinguishable from the term "ring electrode." As used herein, the term "segmented electrode" refers to an electrode of a group of electrodes that are positioned at the same longitudinal location along the longitudinal axis of a lead and that are angularly positioned about the longitudinal axis so they do not overlap and are electrically isolated from one another. For example, at a given position longitudinally along the lead body, three electrodes can be provided with each electrode covering respective segments of less than 120° about the outer diameter of the lead body. By selecting between such electrodes, the electrical field generated by stimulation pulses can be more precisely controlled and, hence, stimulation of undesired tissue can be more easily avoided.

Implementation of segmented electrodes are difficult due to the size of deep brain stimulation leads. Specifically, the outer diameter of deep brain stimulation leads can be approximately 0.06 inches or less. Fabricating electrodes to occupy a fraction of the outside diameter of the lead body and securing the electrodes to the lead body can be quite challenging.

SUMMARY

In one embodiment, a method of fabrication of a stimulation lead comprising a plurality of segmented electrodes for stimulation of tissue of a patient, the method comprises: providing an elongated, substantially cylindrical substrate, the substrate comprising a plurality of recesses defined in an outer surface of the substrate; coating the substrate with conductive material; patterning conductive material on the substrate to form a plurality of electrode surfaces for at least the plurality of segmented electrodes and a plurality of traces connected to the plurality of electrode surfaces, wherein each electrode surface and its corresponding trace are defined in the recesses on the outer surface of the substrate and are electrically isolated from other electrode surfaces and traces; providing insulative material over at least the plurality of traces; and electrically coupling the plurality of traces to conductive wires of a lead body.

The foregoing has outlined rather broadly certain features and/or technical advantages in order that the detailed description that follows may be better understood. Additional features and/or advantages will be described hereinafter which form the subject of the claims. It should be appreciated by those skilled in the art that the conception and specific embodiment disclosed may be readily utilized as a basis for modifying or designing other structures for carrying out the same purposes. It should also be realized by those skilled in the art that such equivalent constructions do not depart from the spirit and scope of the appended claims. The novel features, both as to organization and method of operation, together with further objects and advantages will be better understood from the following description when considered in connection with the accompanying figures. It is to be expressly understood, however, that each of the figures is provided for the purpose of illustration and description only and is not intended as a definition of the limits of the appended claims.

DETAILED DESCRIPTION

The present application is generally related to a process for fabricating a stimulation lead, and more particularly to a process for fabrication of stimulation lead comprising multiple segmented electrodes. In one preferred embodiment, the lead is adapted for deep brain stimulation (DBS). In other embodiments, the lead may be employed for any suitable therapy including spinal cord stimulation (SCS), peripheral nerve stimulation, peripheral nerve field stimulation, cortical stimulation, cardiac therapies, ablation therapies, etc.

FIGS. 1A-1E depict stages of processing in fabrication of a stimulation lead including segmented electrodes according to some representative embodiments.

Figure 1A:
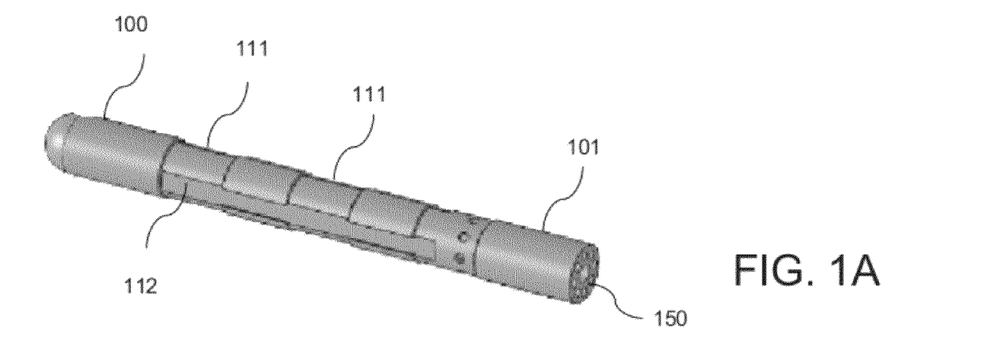
FIGS. 1A-1E depict stages of processing in fabrication of a stimulation lead including segmented electrodes according to some representative embodiments.

FIG. 1A depicts substrate 100 according to one representative embodiment. In one embodiment, substrate 100 is formed from a molded polymer material. Examples of a suitable material for molding substrate 100 include polyetheretherketone (PEEK), liquid crystal polymer (LCP), polyimide, and ceramic materials. In one embodiment, the outside diameter of substrate 100 is approximately 0.06 inches. The outside diameter can be smaller or larger depending upon the intended medical application of substrate 100. For example, for deep brain stimulation, it is clinically beneficial to minimize the outside diameter to reduce tissue trauma during implantation (subject to certain size limitations imposed by current density constraints). Alternatively, other therapies (e.g., peripheral nerve stimulation) may more readily permit greater diameters.

After forming an elongated, substantially cylindrical structure via a molding or other suitable process, additional structural details may be provided on substrate 100 using various machining techniques. For example, recesses 111 may be formed on the outer surface of substrate 100 where electrodes will be subsequently formed. Similarly, one or more recesses (such as recess 112) may be formed where traces will be subsequently formed. The fabrication of electrical components via deposition and plating (see below) in recessed features may enable the electrical components to be more robust against subsequent removal or delamination from substrate 100 after implantation. In some embodiments, channels are laser machined to extend from the proximal end 150 of substrate 100 within the interior of substrate. Other materials and processing may be employed to form substrate 100. For example, substrate 100 could alternatively be implemented using a metallic material that is coated or otherwise covered with a suitable insulator.

Figure 1B:
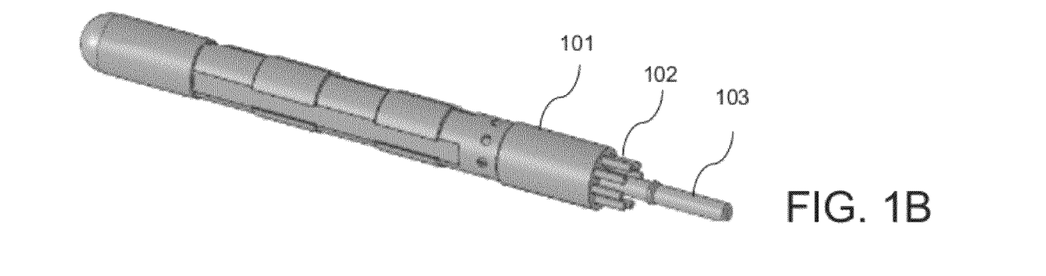
Figure 1C:
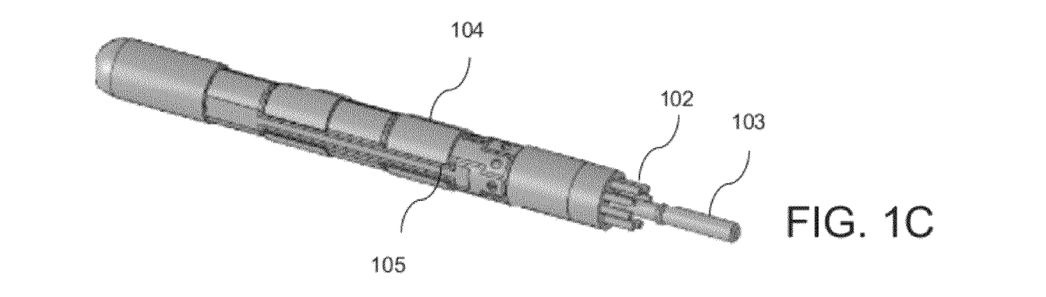

After forming substrate 100, weld tubes 102 and pin 103 are integrated with substrate 100, as shown in FIG. 1B, preferably by providing tubes 102 and pin 103 within channels previously machined into substrate 100. Pin 103 is preferably adapted to strengthen the connection of the fabricated electrode tip portion with the lead body. Pin 103 may also reduce the strain on subsequently added wire connections. The embodiment shown in FIG. 1B, weld tubes 102 are evenly disposed about the circumference of the proximal end of substrate 100. Subsequently, weld tubes 102 will be utilized to facilitate electrical couplings with wire conductors. Weld tubes 102 may possess an outer diameter of approximately 0.080 to 0.010 inches. The wall thickness of approximately 0.0015 to 0.0020 inches. Weld tubes 102 may be fabricated using suitable metal material for implant devices such as 316 stainless steel and MP35N. Such tubes are commercially available from K-tube Corporation (Poway, Calif.) and Small Parts, Inc. (Miramar, Fla.). Vias may be provided to provide access through an exterior portion of substrate to a selected portion of each weld tube 102 to facilitate subsequent electrical coupling between electrical traces and respective weld tubes 102. Vias are preferably initially machined into substrate 100 (see FIG. 1A) before receipt of weld tubes 102, although the vias may be provided at any suitable time.

To begin adding additional electrical components to substrate 100, vapor deposition is preferably applied to cover the exterior surface of substrate 100 with conductive material. In one embodiment, a first layer of titanium is initially vapor deposited and a second layer of gold is vapor deposited over the first layer. Also, as the vapor deposition is applied, conductive material is applied into the vias and, thereby, the deposited conductive material electrically connects weld tubes 102 to conductive material on the surface of substrate 100. Although vapor deposition is discussed according to one embodiment, other processes may be employed such as sputtering. Plating processes may also be employed.

After vapor deposition of the conductive material, electrode surfaces 104 and electrode traces 105 from the proximal end of substrate 100 to those electrode surfaces are formed by removing conductive material from selected portions of the exterior surface of substrate 100 to define electrically isolated features on the exterior surface. During the removal process, conductive material is left on the surface of substrate 100 that is in electrical contact with the conductive material in the vias to the weld tubes 102. Also, it is noted that only one electrode surface 104 and trace 105 are annotated in FIG. 1C for the sake of clarity. In one embodiment, laser ablation of the conductive material is employed to define the various, electrically isolated features. After defining the electrically isolated features, additional conductive material is provided to build up the depth of the electrode surfaces 104 and traces 105. In one embodiment, electrode plating of gold is initially applied and then platinum is plated over the gold. Although laser ablation is one process suitable for defining electrode surfaces and traces, masking and etching processes or any other suitable processes could be alternatively employed.

An exterior insulative surface is provided for the purpose of electrically insulating traces 105. The surface is preferably applied by dip coating the tip assembly in suitable insulative biocompatible material such as paralyne or BIONATE™ resin (a thermoplastic polycarbonate urethane). Spray coating may also be employed. The deposited conductive surfaces are exposed through the insulative material (using laser ablation or any suitable method) to form segmented electrodes 106, tip electrode 110, and ring electrode 107. After exposure of electrodes 106, 110, and 107, stimulation tip 150 is ready to be integrated with a lead body to form a directional stimulation lead for neurostimulation or other suitable medical therapy. The pre-fabricated lead body may already comprise terminals (electrical contacts intended for receiving electrical pulses) at the proximal end of the lead body. Alternatively, terminals may be provided after integration of the lead body with the stimulation tip. In one embodiment, ring electrode 107 substantially circumscribes the outer diameter of tip 150, but is not completely continuous about the outer diameter of tip 150. A "slit" may be provided in ring electrode 107 to accommodate passage of the traces for the other electrodes 106 and 110.

Figure 1D:
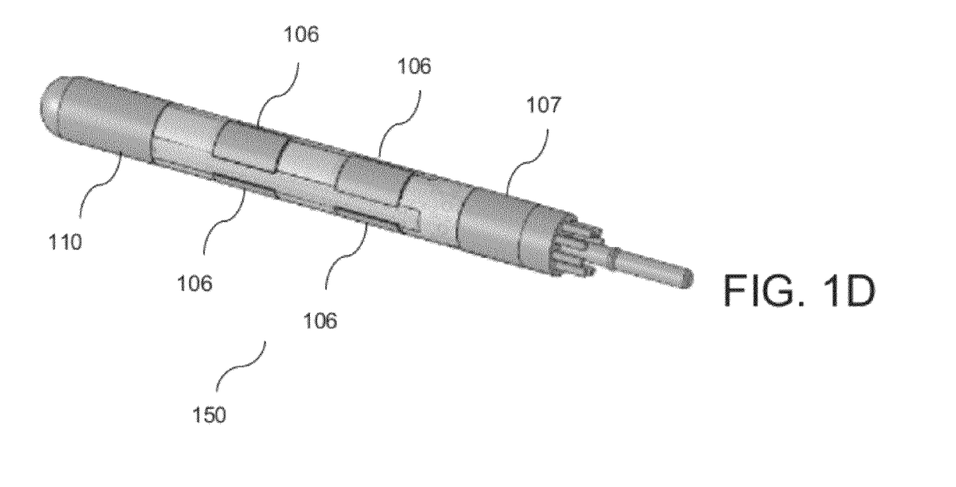
Figure 1E:
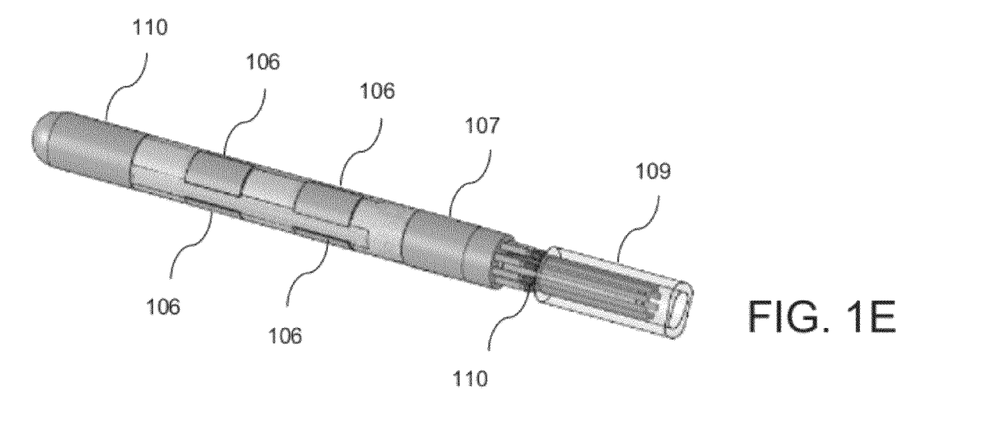

As shown in FIG. 1D, conductive wires 110 of a pre-fabricated lead body are inserted within weld tubes 102 of stimulation tip 150 and are electrically and mechanically coupled to weld tubes 102 using laser welding as an example. Due to the electrical coupling with weld tubes 102, each conductive wire 110 is, in turn, electrically coupled to tip electrode 110, ring electrode 106, or one of the segmented electrodes 104. Insulative material 109 is preferably provided over the welding area. Over-molding is preferably employed to provide the insulative material according to one representative embodiment as shown in FIG. 1E. Centerless grinding or other suitable processing may be provided to remove any excess molded material and to obtain a uniform diameter.

Figure 2A:
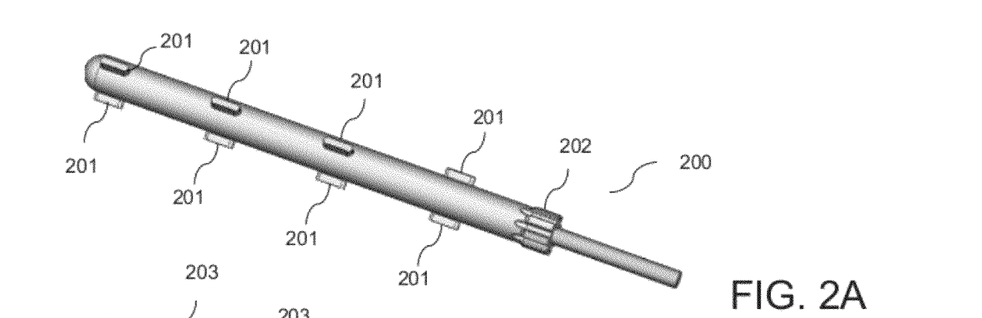
FIGS. 2A-2G depict stages of processing in fabrication of a stimulation lead including segmented electrodes according to some representative embodiments.

Referring to FIG. 2A, other designs may be employed for a substrate when fabricating a stimulation lead having segmented electrodes. As shown in FIG. 2A, substrate 200 comprises a first set of plurality of projections 201 along the length of and about the circumference of outer surface of substrate 200. Also, as shown in FIG. 2A, substrate 200 comprises a second set of projections 202 disposed about the circumference of the proximal end of substrate 200.

Figure 2B:
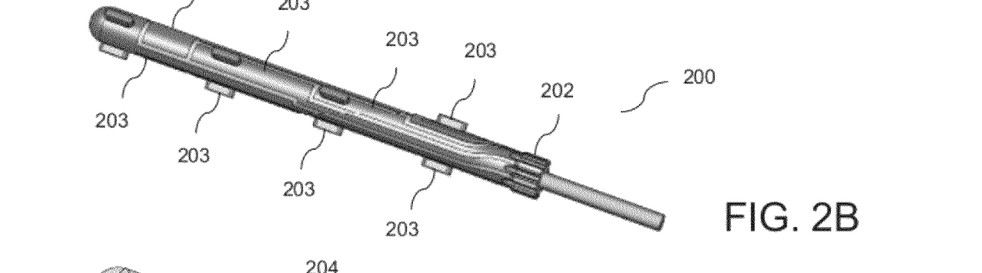

During the fabrication process of a stimulation lead, a layer of conductive material is preferably sputtered or vapor deposited onto substrate 200. The layer of conductive material is then patterned to define a plurality of electrically isolated features 203 with each trace coupling a respective projection 201 with a corresponding projection 202 at the proximal end of substrate 200 (as shown in FIG. 2B). Laser ablation is preferably employed to ablate conductive material to define the separate electrical features on the surface of substrate 200.

Figure 2C:
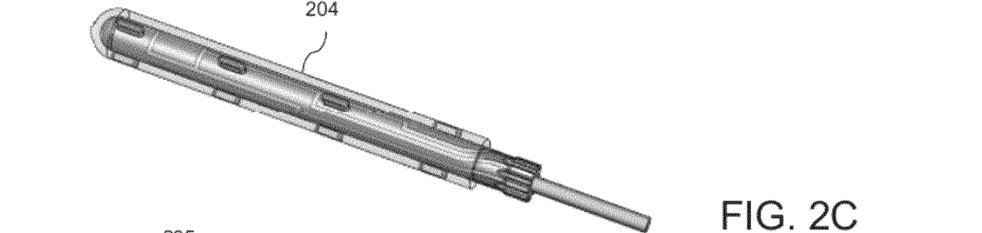

Insulative surface 204 (as shown in FIG. 2C) is applied over features 203. Any suitable biocompatible material may be employed such as polycarbonate urethanes and silicone polyether urethanes as examples. Preferably, an over-molding process is employed. In some embodiments, the distal tips or upper portions of projections 201 are not encapsulated by the molded material leaving a portion of exposed conductive material.

Figure 2D:
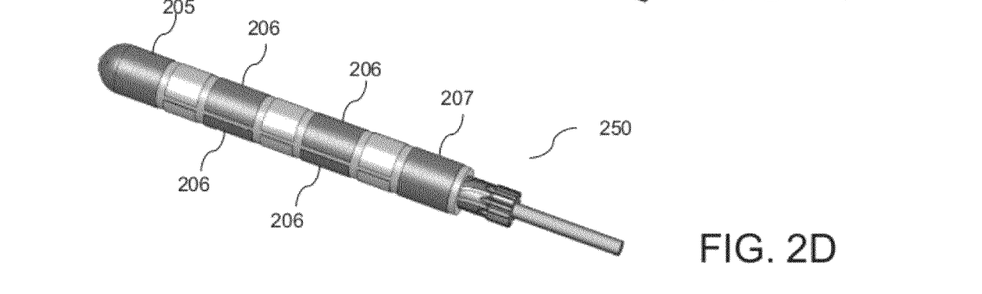

Tip electrode 205, segmented electrodes 206, and ring electrode 207 (or a "c-shaped" electrode) are provided over insulative material 204 to form stimulation tip 250 as shown in FIG. 2D. The provision of the electrodes may employ vapor deposition, ablation, and plating in a similar manner discussed above in regard to stimulation tip 250. The electrodes 205-207 are electrically coupled to features 203 underneath insulative material through the conductive material applied to projections 201.

Figures 2E, 2F:
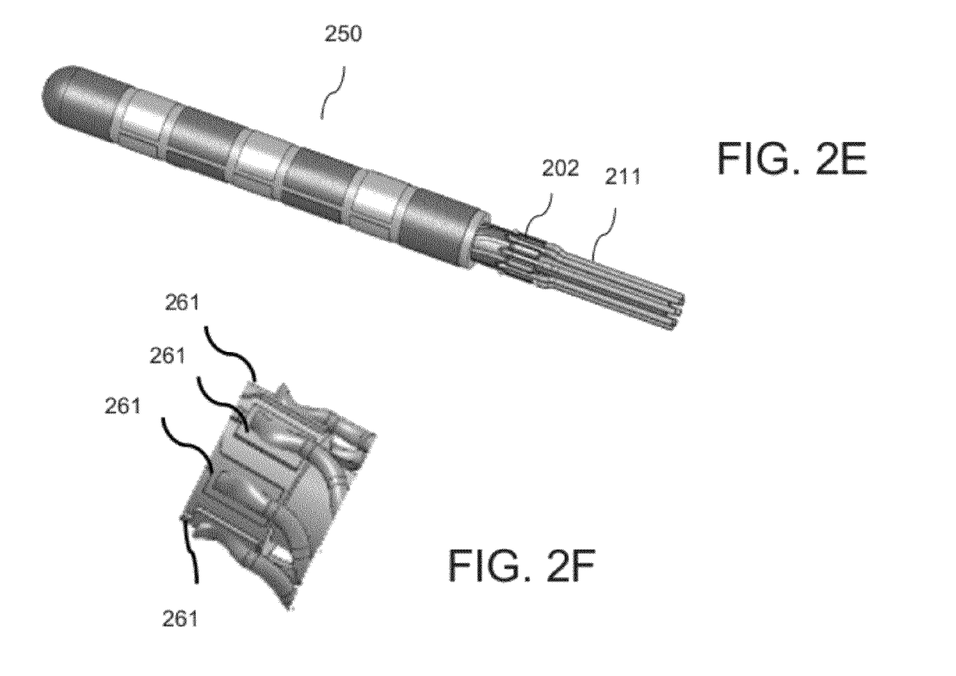

Stimulation tip 250 is then ready to be integrated with lead body to form a stimulation lead. In one embodiment, as shown in FIG. 2E, wires 211 of a lead body are welded to the conductive material applied to respective projections 202 of substrate 200. In another embodiment shown in FIG. 2F, in lieu of projections 202, planar bonding structures 261, which are electrically coupled to deposited traces, are provided on the exterior surface of substrate 200 (or any other suitable substrate) for being electrically coupled to conductive wires.

Figure 2G:
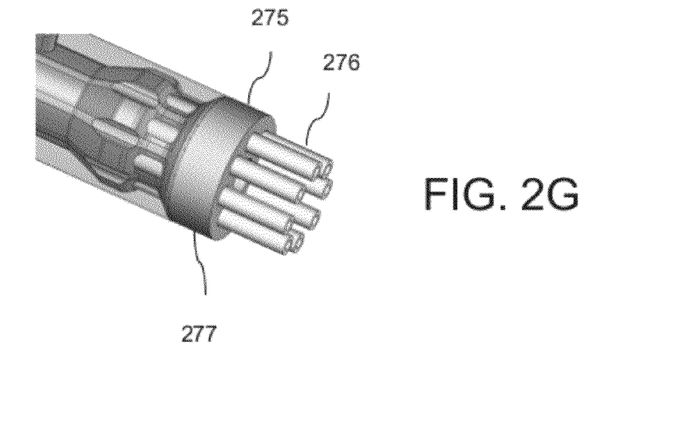

In other embodiments, weld tubes 276 of a pre-formed fixture 275 (shown in FIG. 2G) are electrically coupled to the conductive material applied to the distal end of a respective substrate. In one embodiment, the pre-formed fixture 275 is mechanically coupled to the substrate and conductive material of the applied traces is applied over weld tubes 276 of fixture 275. Conductive wires of a lead body may then be laser welded within each weld tube 276 of fixture 275. Annular portion 277 of fixture 275 is adapted to hold each weld tube 276 in a predefined position. Annular portion 277 is preferably formed using a suitable biocompatible insulative material. In a preferred embodiment, annular portion 277 is formed of a insulative material capable of reflow for integration or fusing with other insulative material of the lead. Over-molding may then be performed over the wires and grinding performed to remove any excess material. The over-molding process may cause annular portion 277 to be placed in a state of flow thereby causing its insulative material to be fused with other insulative material of the lead.

Figure 3:
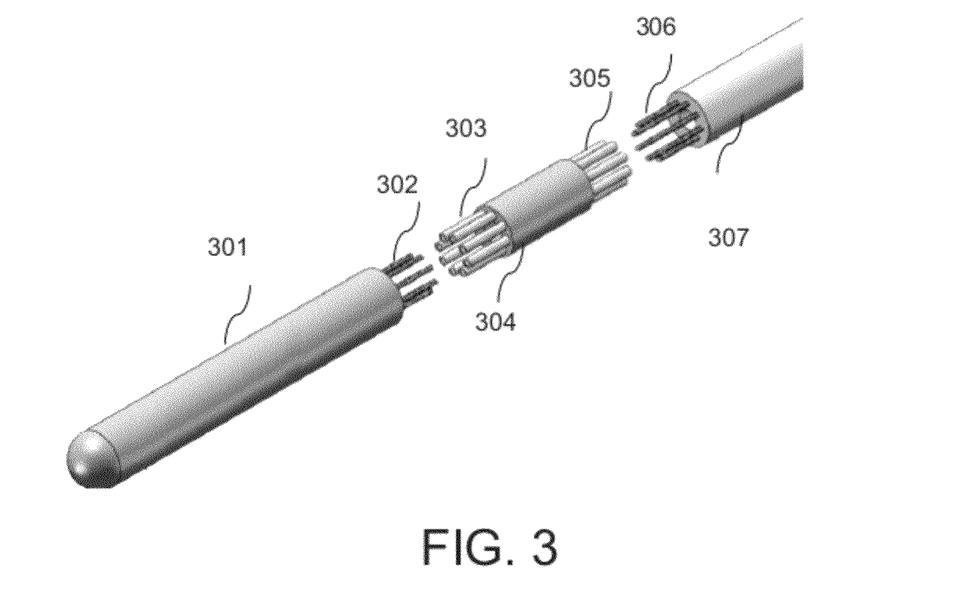
FIG. 3 depicts a mechanism for interconnecting a stimulation tip with a lead body according to some embodiments.

FIG. 3 depicts another mechanism that may be employed to interconnect stimulation tip 301 with lead body 307 according to some embodiments. Stimulation tip 301 may comprise a suitable number and pattern of electrodes, including but not limited to tip electrodes, ring electrodes and/or segmented electrodes (not shown). The electrodes of stimulation tip 301 are electrically connected to wires 302 of the stimulation tip which are exposed at the proximal end of stimulation tip 301. Lead body 307 also comprises a plurality of exposed wires 306 which are located at the distal end of lead body 307. Fixture 304 is employed to interconnect stimulation tip 301 and lead body 307. Fixture 304 is similar to fixture 275 except that weld tubes of fixture 304 extend from both ends of fixture 304. During fabrication of a stimulation lead, wires 302 are placed with first end 303 of fixture 304 and laser welded thereto. Similarly, wires 306 of lead body 307 are inserted in the other end of the weld tubes of fixture 304 and laser welded thereto.

Although the connection structures and processes discussed herein are advantageous for segmented electrode stimulation lead fabrication, the structures and processes may be employed to provide interconnection for any type of stimulation lead. For example, a lead body may be interconnected to a paddle structure for a paddle-style lead. In another example embodiment, custom fabricated leads having electrode leads (in linear or planar form) can be fabricated for a particular patient and interconnected with a lead body to form a custom stimulation lead for that patient. For example, an electrode layout may be selected for a cortical paddle-style stimulation lead for a patient based upon imaging of the patient's cortical physiology and/or cortical neuronal activity.

Figure 4:
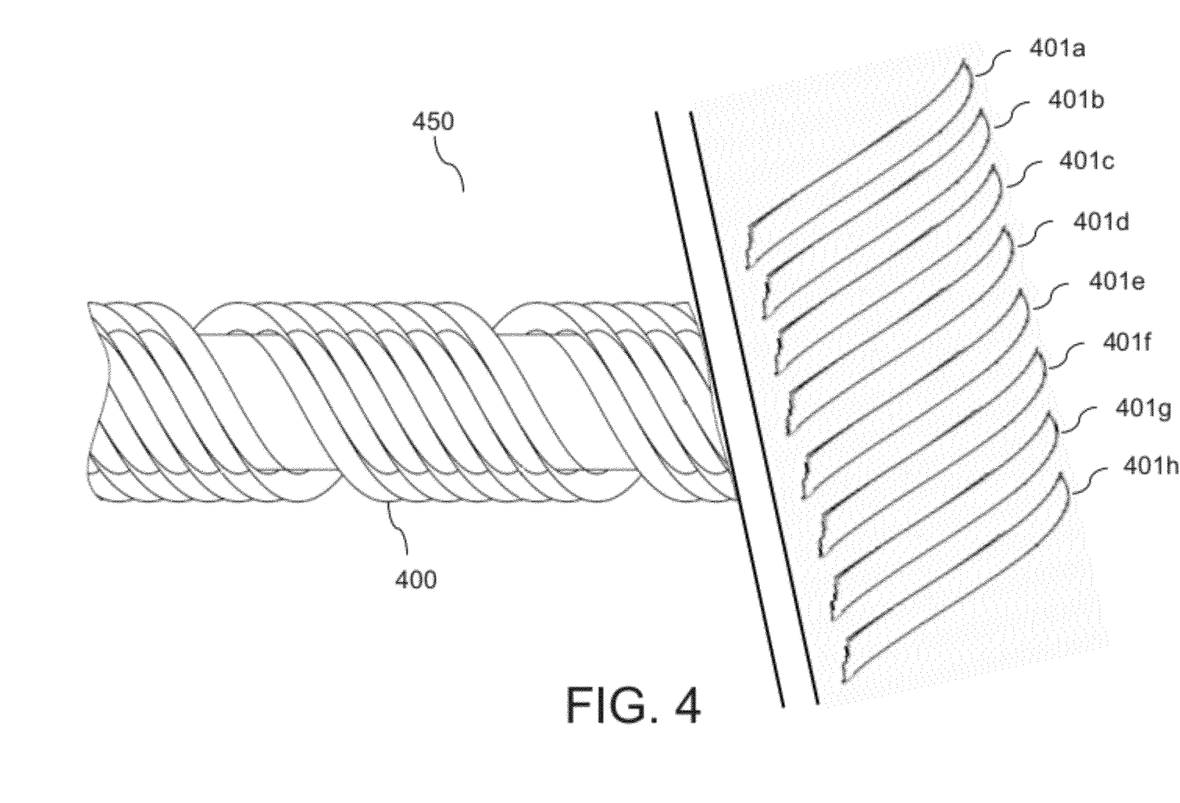
FIG. 4 depicts a lead body assembly for attachment to a stimulation tip according to some representative embodiments.

FIG. 4 depicts intermediate lead body assembly 450 adapted for connection to a stimulation tip according to one representative embodiment. Lead body assembly 450 comprises lead body 400 with a suitable number of conductors (shown individually as conductors 401a-401h) embedded or otherwise enclosed within insulative material. Conductors 401 are provided to conduct electrical pulses from the proximal end of lead assembly 450 to the distal end of lead assembly 450. Lead body 400 may be fabricated using any known or later developed processes. Examples of various lead body fabrication processes are disclosed in U.S. Pat. No. 6,216,045, U.S. Pat. No. 7,287,366, U.S. Patent Application Publication No. 20050027340A1, and U.S. Patent Application Publication No. 20070282411A1, which are incorporated herein by reference.

As is known in the art, each individual conductor 401 is commonly provided with a thin coating of a different insulator such as perfluoroalkoxyethylene (PFA). The purpose of the different coating is to ensure that the wire within the conductor 401 remains insulated in the event that the other polymer material of the lead body 400 is breached or otherwise fails while the lead body 400 is implanted within a patient. The conductors 401 are commonly helically wound and insulative material (e.g., a polyurethane, PURSIL®, CARBOSIL®, etc.) is applied over the conductors to hold conductors 401 in place and to support conductors 401. Other common types of lead bodies provide individually coiled conductors within separate lumens of a lead body. Such lead bodies may also be utilized according to some embodiments.

As shown in FIG. 4, the outer insulative material of the lead body 400 is removed at the distal end of lead body 400 to permit access to a length of each conductor 401. For example, a suitable laser (e.g., a UV laser) can be used to remove the insulative material over a controlled portion of the preformed lead body 400 to release a length of each conductor 401 from lead body 400. Alternatively, manual stripping may be performed to release each conductor 401. Depending upon the type of harder insulative material applied to each individual conductor 401, a separate process may be used to further expose a conductive portion of the wire of each conductor. Lead body assembly 450 may then be electrically coupled to a suitable stimulation tip.

Terminals, electrical contacts for receiving electrical pulses, (not shown) are also provided on the proximal end of the lead body where the terminals are electrically coupled to the conductive wires internal to the lead body. The terminals may be provided before or after integration of the lead body with a stimulation tip. The terminals may be provided using any known or later developed fabrication process. An example of the suitable fabrication process is shown in U.S. Pat. No. 6,216,045.

Figure 5A:
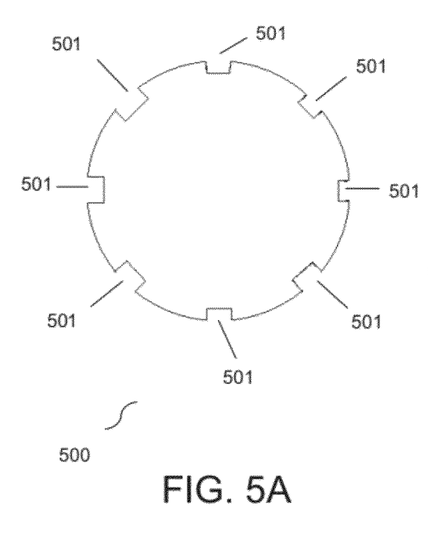
FIG. 5A-5D depict cross-sectional views of a stimulation tip during fabrication of segmented electrodes according to some representative embodiments.

In other embodiments, a substrate for a stimulation lead is initially machined or otherwise patterned to define metallization areas for subsequent provision of traces and electrodes. For fabrication of a directional lead, an elongated, substantially cylindrical substrate is initially provided. Examples of a suitable material for the substrate include polyetheretherketone (PEEK), liquid crystal polymer (LCP), polyimide, and ceramic materials. As shown in FIG. 5A, laser machining is provided to define channels or grooves 501 extending from a proximal end of substrate 500 to locations where electrodes will be fabricated. FIG. 5A depicts a cross-sectional view of substrate 500 at one axial location along the length of substrate 500. Moving along the axial direction, channels or grooves 501 may include one or more turns or bends to route channels or grooves in a manner to avoid crossing areas designated for other electrical components that are intended to be electrically isolated. Alternatively, channels or grooves 501 may extend in a substantially linear manner along the length of the substrate with each channel or groove 501 distributed about the circumference of the substrate 500 (evenly or unevenly).

Figure 5B:
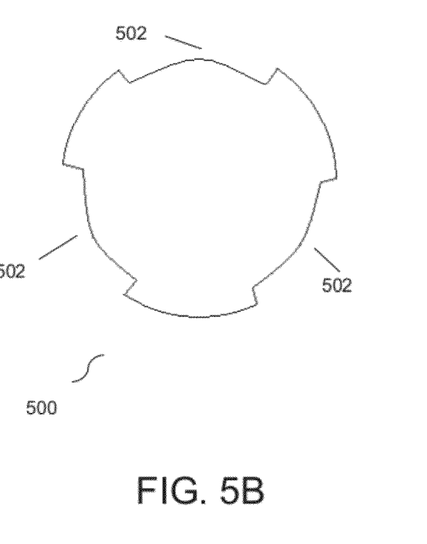

As shown in FIG. 5B, areas 502 for fabrication of electrodes are provided in a similar manner. Each area 502 is connected to a corresponding groove or channel 501. FIG. 5B depicts a cross-sectional view of substrate 500 at one axial location. At the shown axial location, three segmented electrodes will be provided. Areas 502 are provided with center-to-center spacings of 120° to evenly circumscribe substrate 500, although other spacings could be employed. Any suitable number of segmented electrodes could be provided about the circumference of substrate 500 at any given axial location. Also, areas for other groups of segmented electrodes, ring electrodes, and/or a tip electrode could be defined by removal of material from substrate 500 at other axial locations.

In one embodiment, bond pad locations are machined at the proximal end of substrate 500 in a similar manner and bond pads are attached at those locations. The bond pads may be provided for the purpose of facilitating bonding of conductive wires in electrical contact with traces of the completed stimulation tip.

After defining features into the surface of substrate 500, conductive material is provided to substrate 500. For example, vapor deposition or sputtering processes could be provided to metalize the surface of substrate 500. In one embodiment, gold is initially applied over substrate 500. In another embodiment, titanium is initially applied and gold is applied over the titanium layer.

After metalizing the surface of substrate 500, substrate 500 is subjected to a grinding process (e.g., centerless grinding) or other suitable process to remove the conductive material on the very outer surface of substrate 500. The grinding or other process leaves the conductive material within the features defined within the surface of substrate 500. That is, the conductive material within grooves or channels 501 and electrode areas 502 is left unaffected. After the grinding is performed, each electrode area 502 and its respective groove 501 are electrically isolated.

Figure 5C:
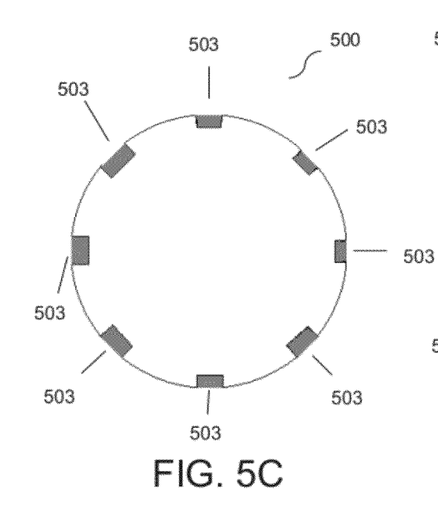
Figure 5D:
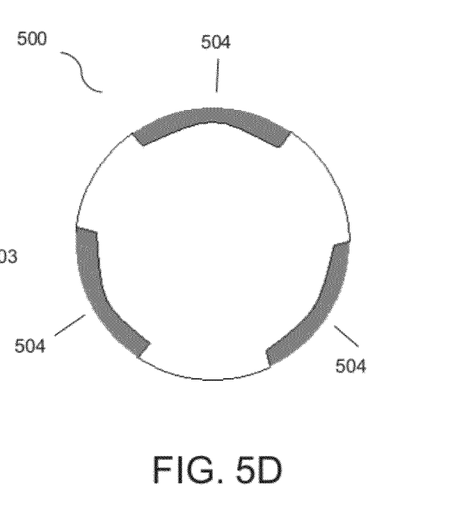

Electrode plating is then preferably applied to thicken the conductive material. Preferably, platinum is plated over the deposited gold. FIG. 5C depicts a cross-sectional view of substrate 500 at one axial location after provision of the conductive material. As shown in FIG. 5C, traces 503, within the grooves 502 provided within the surface of substrate 500, are formed by the conductive material. FIG. 5D depicts another cross-sectional view of substrate 500 at another axial location after provision of the conductive material. As shown in FIG. 5D, segmented electrodes 504, within electrode areas 502 provided within the surface of substrate 500, are formed by the conductive material. Also, each segmented electrode 504 is electrically coupled to a respective trace 503 that extends to the proximal end of substrate 500.

An insulator layer is provided. Over-molding or dip coating may be utilized as examples. The conductive material of the electrodes is exposed through the applied insulator layer. For example, laser ablation of the insulative material may be employed. At this point, the stimulation tip is completed and is ready for integration with a lead body using any suitable interconnection structures and/or processes such as those discussed herein.

Variations of lead fabrication by machining or otherwise providing features within a substrate are possible. In one alternative embodiment, traces are initially provided and over-molding is performed. Areas for electrode fabrication may then be formed over the over-molding above the layer comprising the electrical traces. Vias may also be created at the electrode areas to the traces. Then, metallization (vapor deposition, sputtering, plating, etc.) of the electrode areas is performed to complete the stimulation tip.

Figure 6A:
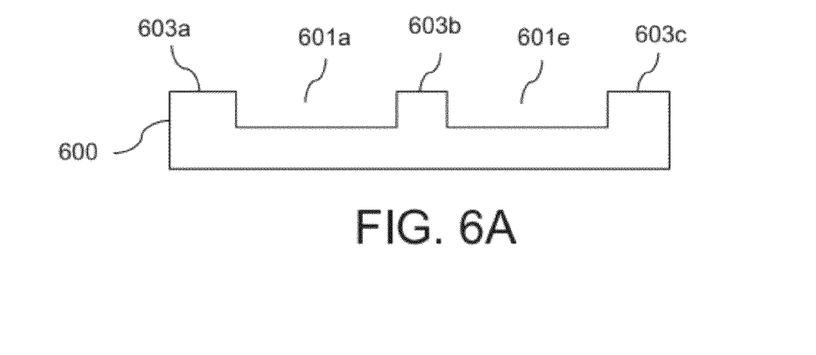
FIGS. 6A and 6B depict a planar substrate with recess for formation of electrodes and trenches for formation of traces for electrical connection to the electrodes according to some representative embodiments.
Figure 6B:
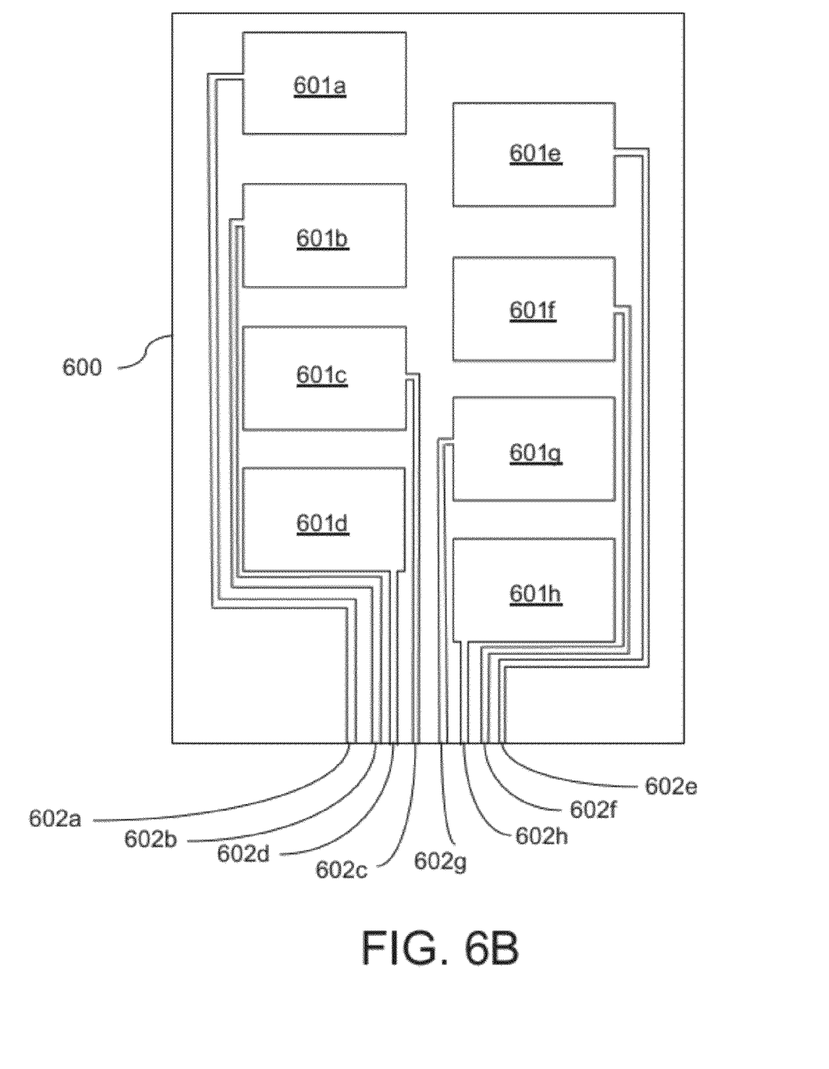

In another embodiment, a similar process may be employed to fabricate a stimulation paddle for a paddle-style stimulation lead. As shown in FIGS. 6A and 6B, a substrate 600 would be shaped in a manner similar to known stimulation paddles and the various components would be fabricated in a substantially planar arrangement (in one or more layers). In a preferred embodiment, recesses 601a-601h are provided in substrate to provide locations where electrodes will be fabricated. Also, trenches 602a-602g are provided from a proximal end of substrate 600 which each connect to respective one of recesses 602a-602h. In one embodiment, recesses 601a-601h and trenches 602a-602h are provided by laser machining substrate 600. In another embodiment, molding techniques may be provided to define the various features. The pattern of recesses 602a-602h and trenches 602a-602h shown in FIGS. 6A and 6B are provided as one example. Any suitable pattern, arrangement, and number of such features may be selected according to some embodiments.

After forming the features into the surface of substrate 600, deposition of conductive material is performed using any suitable process. After deposition, a grinding, machining, or other suitable process is performed to remove conductive material from the outer surface of substrate 600 while leaving conductive material within the features defined below the outer surface. For example, as shown in FIG. 6A, conductive material is removed from surfaces 603a-603c while conductive material is left within recesses 601a and 601e. The removal of conductive material from the exterior surfaces of substrate 600 leaves the various electrical components electrically isolated from each other. Further conductive material may be provided using, for example, a plating process. The electrodes and electrical traces are thereby formed on a paddle structure. The formed paddle structure is then integrated with a lead body using any suitable technique, such as those discussed herein.

In another embodiment, stimulation paddles are fabricated in a batch manner. That is, a relative large substrate is provided and multiple sets of recesses and trenches are formed across the substrate. The deposition of conductive material, removal of conductive material, and plating is performed for the entire substrate. At that point, individual paddles may be obtained from cutting through the substrate or otherwise separating between the various sets of formed electrodes and trenches. Further processing on the removed paddles may occur, e.g., to define curved edges or any other suitable feature. Grinding, machining, or other mechanical shaping processing may be applied. Alternative, suitable molding techniques could employed to define additional features on the paddle.

During the foregoing discussion, certain fabrication steps have been discussed in a particular sequence. The sequence discussed herein has been presented for the convenience of the reader. It shall be appreciated that the discussed sequence is not required and any suitable order of fabrication may be performed without departing from the scope of the application. Moreover, certain steps may be performed concurrently or separately. For example, grinding may be applied to certain segments of the lead separately or grinding may be applied simultaneously to multiple segments.

Figure 7A:
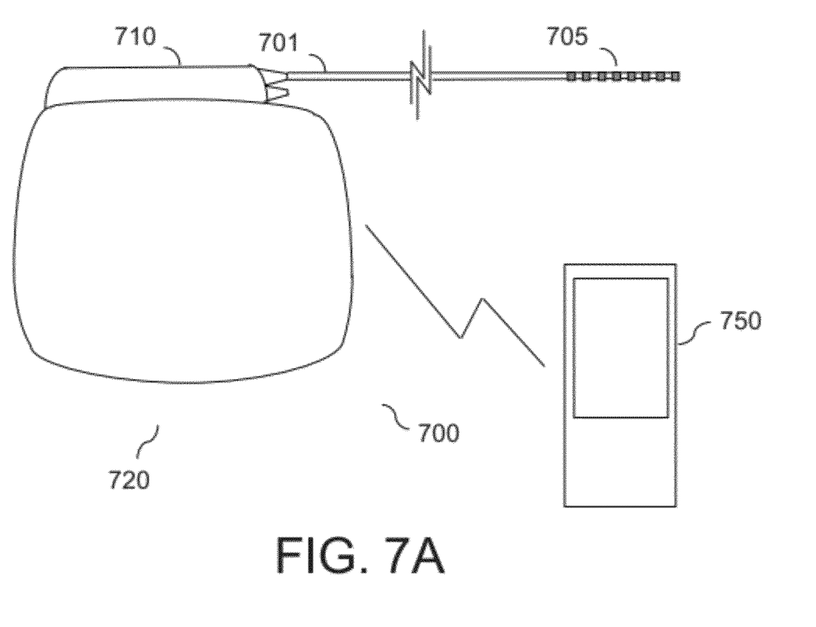
FIG. 7A depicts a stimulation system including a segmented stimulation lead and FIG. 7B depicts a segmented electrode stimulation lead for use in the system of FIG. 7A according to embodiments disclosed herein.

FIG. 7A depicts stimulation system 700 according to one representative embodiment. Neurostimulation system 700 includes pulse generator 720 and one or more stimulation leads 701. Examples of commercially available pulse generator include the EON™, EON MINI™, and the LIBRA™ pulse generators available from St. Jude Medical Neuromodulation Division. Pulse generator 720 is typically implemented using a metallic housing that encloses circuitry for generating the electrical pulses for application to neural tissue of the patient. Control circuitry, communication circuitry, and a rechargeable battery (not shown) are also typically included within pulse generator 720. Pulse generator 720 is usually implanted within a subcutaneous pocket created under the skin by a physician.

Lead 701 is electrically coupled to the circuitry within pulse generator 720 using header 710. Lead 701 includes terminals (not shown) that are adapted to electrically connect with electrical connectors (e.g., "Bal-Seal" connectors which are commercially available and widely known) disposed within header 710. The terminals are electrically coupled to conductors (not shown) within the lead body of lead 701. The conductors conduct pulses from the proximal end to the distal end of lead 701. The conductors are also electrically coupled to electrodes 705 to apply the pulses to tissue of the patient. Lead 701 can be utilized for any suitable stimulation therapy. For example, the distal end of lead 701 may be implanted within a deep brain location or a cortical location for stimulation of brain tissue. The distal end of lead 701 may be implanted in a subcutaneous location for stimulation of a peripheral nerve or peripheral nerve fibers. Alternatively, the distal end of lead 701 may be positioned within the epidural space of a patient. Although some embodiments are adapted for stimulation of neural tissue of the patient, other embodiments may stimulate any suitable tissue of a patient (such as cardiac tissue). An "extension" lead (not shown) may be utilized as an intermediate connector if deemed appropriate by the physician.

Figure 7B:
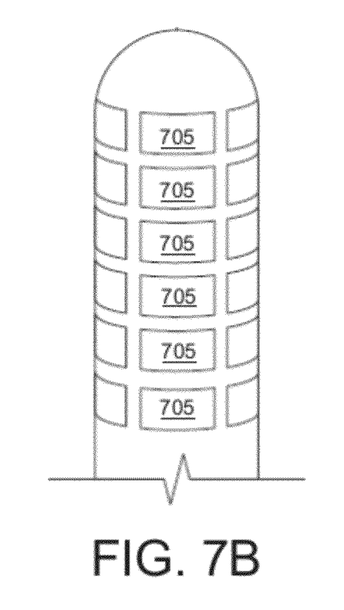

Electrodes 705 include multiple segmented electrodes as shown in FIG. 7B. The use of segmented electrodes permits the clinician to more precisely control the electrical field generated by the stimulation pulses and, hence, to more precisely control the stimulation effect in surrounding tissue. Electrodes 705 may also include one or more ring electrodes or a tip electrode (not shown in FIG. 7B). Any of the electrode assemblies and segmented electrodes discussed herein can be used for the fabrication of electrodes 705. Electrodes 705 may be utilized to electrically stimulate any suitable tissue within the body including, but not limited to, brain tissue, tissue of the spinal cord, peripheral nerves or peripheral nerve fibers, digestive tissue, cardiac tissue, etc. Electrodes 705 may also be additionally or alternatively utilized to sense electrical potentials in any suitable tissue within a patient's body.

Pulse generator 720 preferably wirelessly communicates with programmer device 750. Programmer device 750 enables a clinician to control the pulse generating operations of pulse generator 720. The clinician can select electrode combinations, pulse amplitude, pulse width, frequency parameters, and/or the like using the user interface of programmer device 750. The parameters can be defined in terms of "stim sets," "stimulation programs," (which are known in the art) or any other suitable format. Programmer device 750 responds by communicating the parameters to pulse generator 720 and pulse generator 720 modifies its operations to generate stimulation pulses according to the communicated parameters.

Although certain representative embodiments and advantages have been described in detail, it should be understood that various changes, substitutions and alterations can be made herein without departing from the spirit and scope of the appended claims. Moreover, the scope of the present application is not intended to be limited to the particular embodiments of the process, machine, manufacture, composition of matter, means, methods and steps described in the specification. As one of ordinary skill in the art will readily appreciate when reading the present application, other processes, machines, manufacture, compositions of matter, means, methods, or steps, presently existing or later to be developed that perform substantially the same function or achieve substantially the same result as the described embodiments may be utilized. Accordingly, the appended claims are intended to include within their scope such processes, machines, manufacture, compositions of matter, means, methods, or steps.

What is claimed is:

1. A method of fabrication of a stimulation lead comprising a plurality of segmented electrodes for stimulation of tissue of a patient, the method comprising:
   providing a substrate, the substrate comprising a plurality of recesses defined in an outer surface of the substrate;
   coating the substrate with conductive material, the coating including vapor depositing a first conductive material and subsequent to the deposition of the first conductive material, vapor depositing a second conductive material;

patterning conductive material on the substrate to form a plurality of electrode surfaces for at least the plurality of segmented electrodes and a plurality of traces connected to the plurality of electrode surfaces, wherein each electrode surface and its corresponding trace are defined in the recesses on the outer surface of the substrate and are electrically isolated from other electrode surfaces and traces;

providing insulative material over at least the plurality of traces; and electrically coupling the plurality of traces to conductive wires of a lead body.

2. The method of claim 1 further comprising:
providing a plurality of weld tubes at a proximal end of the substrate;
wherein the electrically coupling comprises welding the conductive wires to the plurality of weld tubes.

3. The method of claim 2 wherein the substrate comprises a plurality of vias with conductive material disposed in the vias, the conductive material in the plurality of vias electrically connecting conductive material of the electrode surfaces with the plurality of weld tubes.

4. The method of claim 1 wherein the electrically coupling comprises welding the conductive wires to the plurality of traces.

5. The method of claim 1 wherein the patterning comprises laser ablating conductive material from the substrate.

6. The method of claim 1 wherein the coating further comprises:
subsequent to vapor deposition of conductive material, plating conductive material over the vapor deposited conductive material.

7. The method of claim 6 wherein the plated conductive material is platinum.

8. The method of claim 1 wherein the plurality of electrode surfaces further comprise surfaces for a tip electrode and ring electrode.

9. A method of fabrication of a stimulation lead comprising a plurality of segmented electrodes for stimulation of tissue of a patient, the method comprising:
providing a substrate, the substrate comprising (i) a plurality of recesses defined in an outer surface of the substrate and (ii) a plurality of apertures, at a proximal end of the substrate, extending longitudinally within the substrate;
coating the substrate with conductive material, the coating including vapor depositing a first conductive material and subsequent to the deposition of the first conductive material, vapor depositing a second conductive material;
patterning conductive material on the substrate to form a plurality of electrode surfaces for at least the plurality of segmented electrodes and a plurality of traces connected to the plurality of electrode surfaces, wherein each electrode surface and its corresponding trace are defined in the recesses on the outer surface of the substrate and are electrically isolated from other electrode surfaces and traces;
providing insulative material over at least the plurality of traces; and
electrically coupling the plurality of traces to conductive wires of a lead body through the plurality of apertures at the proximal end of the substrate.

10. The method of claim 9 further comprising:
inserting a pin within a central aperture defined in the proximal end of the substrate.

11. The method of claim 9 further comprising:
providing a plurality of weld tubes within the plurality of apertures at a proximal end of the substrate;
wherein the electrically coupling comprises welding the conductive wires to the plurality of weld tubes.

12. The method of claim 11 wherein the substrate comprises a plurality of vias with conductive material disposed in the vias, the conductive material in the plurality of vias electrically connecting conductive material of the electrode surfaces with the plurality of weld tubes.

13. The method of claim 9 wherein the patterning comprises laser ablating conductive material from the substrate.

14. The method of claim 9 wherein the coating further comprises:
subsequent to vapor deposition of conductive material, plating conductive material over the vapor deposited conductive material.

15. The method of claim 14 wherein the plated conductive material is platinum.

16. The method of claim 9 wherein the plurality of electrode surfaces further comprise surfaces for a tip electrode and ring electrode.

17. A method of fabrication of a stimulation lead comprising a plurality of segmented electrodes for stimulation of tissue of a patient, the method comprising:
providing a substrate, the substrate comprising a plurality of recesses defined in an outer surface of the substrate;
coating the substrate with conductive material, the coating including vapor depositing conductive material on the substrate;
subsequent to vapor deposition of conductive material, plating conductive material over the vapor deposited conductive material;
patterning conductive material on the substrate to form a plurality of electrode surfaces for at least the plurality of segmented electrodes and a plurality of traces connected to the plurality of electrode surfaces, wherein each electrode surface and its corresponding trace are defined in the recesses on the outer surface of the substrate and are electrically isolated from other electrode surfaces and traces;
providing insulative material over at least the plurality of traces; and
electrically coupling the plurality of traces to conductive wires of a lead body.

18. The method of claim 17 further comprising:
providing a plurality of weld tubes at a proximal end of the substrate;
wherein the electrically coupling comprises welding the conductive wires to the plurality of weld tubes.

19. The method of claim 18 wherein the substrate comprises a plurality of vias with conductive material disposed in the vias, the conductive material in the plurality of vias electrically connecting conductive material of the electrode surfaces with the plurality of weld tubes.

* * * * *